United States Patent [19]

Picard et al.

[11] Patent Number: 5,254,715
[45] Date of Patent: Oct. 19, 1993

[54] AMINOSULFONYL CARBAMATES

[75] Inventors: Joseph A. Picard; Drago R. Sliskovic, both of Ypsilanti, Mich.

[73] Assignee: Warner-Lambert Company, Morris Plains, N.J.

[21] Appl. No.: 747,031

[22] Filed: Aug. 19, 1991

Related U.S. Application Data

[63] Continuation-in-part of Ser. No. 610,487, Nov. 7, 1990, abandoned.

[51] Int. Cl.$^5$ ............................................. C07C 307/06
[52] U.S. Cl. ...................................... 560/13; 544/159; 544/283; 546/233; 548/491; 548/542; 558/233; 560/134; 560/137; 560/148
[58] Field of Search ............... 558/233; 560/13, 134, 560/137, 148; 544/159, 283; 546/233; 548/491, 542

[56] References Cited

FOREIGN PATENT DOCUMENTS 123763 5/1983 European Pat. Off. .
940292 3/1956 Fed. Rep. of Germany .

OTHER PUBLICATIONS

Phosphorus and Sulfur 19(2), 167–172 (1984), M. Hedayatullah "Syntheses a l'aide d'Heterocumulenes".
Chem. Ber. 96, 56–67 (1963), R. Graf, "Reactions with N-carbonylsulfamic acid chloride [1], II [2]L: Alcohols and phenols",
J. Med. Chem. 8, 781–784 (1965), J. McFarland, "Sulfamylurea Hypoglycemic Agents. III. Tetrasubstituted Sulfamylureas and N-Sulfamylcarbamates".
Tetrahedron Letters 24, (30) 3091–3094 (1983), J. Montero, "Selective Synthesis of Sulfonylureas and Carboxysulfamides a Novel Route to Oxazolidinones".

*Primary Examiner*—Richard L. Raymond
*Attorney, Agent, or Firm*—Ruth H. Newtson; Michael J. Atkins

[57] ABSTRACT

A compound of the following general formula which is useful in treating hypocholesterolemia and atherosclerosis:

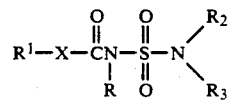

wherein X is oxygen or sulfur; R is hydrogen, alkyl having from 1 to 8 carbon atoms, or benzyl; $R_1$ is phenyl, substituted phenyl, naphthyl, substituted naphthyl, an aralkyl group, a heterocyclic group, or a hydrocarbon chain of from 1 to 20 carbon atoms which is saturated or contains 1 to 3 double bonds and each of $R_2$ and $R_3$ is selected from hydrogen, provided both are not hydrogen, an aralkyl group, a hydrocarbon chain of from 1 to 20 carbon atoms which is saturated or contains 1 to 3 double bonds, an w-substituted alkyl$C_{1-6}$, a heterocyclic group, phenyl, substituted phenyl or $NR_2R_3$ taken together form a monocyclic heterocyclic group.

6 Claims, No Drawings

AMINOSULFONYL CARBAMATES

CROSS-REFERENCE TO RELATED APPLICATION

This application is a continuation-in-part of copending application Ser. No. 07/610,487, filed Nov. 7, 1990, now abandoned.

BACKGROUND OF INVENTION

This invention relates to chemical compounds having pharmacological activity, to pharmaceutical compositions which include these compounds, and to a pharmaceutical method of treatment. More particularly, this invention concerns certain aminosulfonyl carbamates which inhibit the enzyme acyl-coenzyme A:cholesterol acyltransferase (ACAT), pharmaceutical compositions containing these compounds, and a method of treating hypercholesterolemia and atherosclerosis.

In recent years the role which elevated blood plasma levels of cholesterol plays in pathological conditions in man has received much attention. Deposits of cholesterol in the vascular system have been indicated as causative of a variety of pathological conditions including coronary heart disease.

Initially, studies of this problem were directed toward finding therapeutic agents which would be effective in lowering total serum cholesterol levels. It is now known that cholesterol is transported in the blood in the form of complex particles consisting of a core of cholesteryl esters plus triglycerides and an exterior consisting primarily of phospholipids and a variety of types of protein which are recognized by specific receptors. For example, cholesterol is carried to the sites of deposit in blood vessels in the form of low density lipoprotein cholesterol (LDL cholesterol) and away from such sites of deposit by high density lipoprotein cholesterol (HDL cholesterol).

Following these discoveries, the search for therapeutic agents which are more selective in their action: that is, agents which are effective in elevating the blood serum levels of HDL cholesterol and/or lowering the levels of LDL cholesterol. While such agents are effective in moderating the levels of serum cholesterol, they have little or no effect on controlling the initial absorption of dietary cholesterol in the body through the intestinal wall.

In intestinal mucosal cells, dietary cholesterol is absorbed as free cholesterol which must be esterified by the action of the enzyme acyl-CoA:cholesterol acyltransferase (ACAT) before it can be packaged into the chylomicrons which are then released into the blood stream. Thus, therapeutic agents which effectively inhibit the action of ACAT prevent the intestinal absorption of dietary cholesterol into the blood stream or the reabsorption of cholesterol which has been previously released into the intestine through the body's own regulatory action.

INFORMATION DISCLOSURE

Phosphorus and Sulfur 19(2), 167–172 (1984) describes the following compounds as fungicides and bactericides.

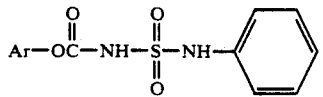

Ar=
2,6-dimethylphenyl
2,6-dimethoxyphenyl
2,6-diisopropylmethyl
2-methyl-6-isopropylphenyl
2,6-di-tert-butylphenyl
2,6-di-tert-butyl-4-methylphenyl
2,4,6-tri-tert-butylphenyl German patent 940,292 dated Mar. 15, 1956 to Farbwerke Hoechst, Ag describes the folloiwng compounds which are said to be useful as textile assistants, pharmaceuticals and pesticides. No specific pharmaceutical utility is described.

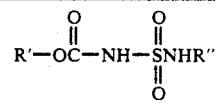

| R' | R'' |
|---|---|
| $C_{12}H_{25}$ | H |
| $C_2H_5$ | 4-$(OC_2H_5)$Ph |
| $C_2H_5$ | Ph |
| $C_2H_5$ | 4-$(COC_2H_5)$Ph |
| $C_{18}H_{35}$ | -4-$(Et_2NCH_2CH_2OC)$—Ph |
| $CH_3$ | Ph |
| $C_2H_5$ | $C_6H_{11}$ |
| $ClCH_2CH_2$ | Ph |
| $ClCH_2CH_2$ | 4-$CH_3$—Ph |
| $C_3H_7$ | $C_3H_7$ |
| i-$C_3H_7$ | $C_6H_{11}$ |
| $CH_2$=$CHCH_2$— | Ph |
| $CH_2$=$CHCH_2$— | $CH_2CH$=$CH_2$ |
| $C_4H_9$ | Ph |
| $C_4H_9$ | $C_6H_{11}$ |
| $C_4H_9$ | H |
| $(Et)_2CHCH_2$ | H |
| $(C_4H_9)(C_2H_5)CHCH_2$ | H |
| $C_6H_{11}$ | Ph |
| Ph—$CH_2$— | $C_3H_7$ |
| Ph | H |
| 4-Cl—Ph | —$CH_2CH$=$CH_2$ |
| $CH_3OCH_2$ | —$CH_2CH$=$CH_2$ |
| Ph—$CH_2$ | 4-$(Et_2CH_2CH_2OC)$—Ph |
| $C_{12}H_{25}$ | 4-$(Et_2CH_2CH_2OC)$—Ph |
| $C_{18}H_{35}$ | $CH_2CH_2NEt_2$ |

Chem. Ber. 96,56–67 (1963) describes compounds of the following formula. No utility for these compounds is disclosed.

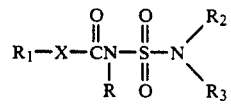

Formula I wherein X is sulfur or oxygen;
wherein R is hydrogen, a straight or branched alkyl having from 1 to 8 carbon atoms, or benzyl;
wherein $R_1$ is
(a) phenyl which is unsubstituted or is substituted with from one to three substituents selected from:
phenyl,
alkyl having from one to six carbon atoms and which is straight or branched,
alkoxy having from one to six carbon atoms and which is straight or branched,
phenoxy,
hydroxy,
fluorine,
chlorine,
bromine,
nitro,
trifluoromethyl,
—COOH,
—COOalkyl wherein alkyl has from one to four carbon atoms and which is straight or branched,
—$(CH_2)_p NR_4 R_5$ wherein p is zero or one, and each of $R_4$ and $R_5$ is hydrogen or a straight or branched alkyl group having one to four carbon atoms;
(b) 1- or 2-naphthyl which is unsubstituted or substituted with one to three substituents selected from phenyl,
alkyl having from one to six carbon atoms and which is straight or branched,
alkoxy having from one to six carbon atoms and which is straight or branched,
hydroxy,
phenoxy,
fluorine,
chlorine,
bromine,
nitro,
trifluoromethyl,
—COOH,
—COOalkyl wherein alkyl has from one to four carbon atoms and is straight or branched,
—$(CH_2)_p NR_4 R_5$ wherein p, $R_4$, and $R_5$ have the meanings defined above;
(c) the group

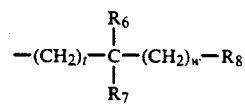

wherein t is zero or one to four; w is zero or one to four with the proviso that the sum of t and w is not greater than five; $R_6$ and $R_7$ are independently selected from hydrogen or alkyl having for one to six carbon atoms, or when $R_6$ is hydrogen, $R_7$ can be selected from the groups defined for $R_8$; and $R_8$ is phenyl or phenyl substituted with from one to three substituents selected from straight or branched alkyl having from one to six carbon atoms, straight or branched alkoxy having from

---

| R | R' | R'' |
|---|----|-----|
| $CH_3$ | H | Ph |
| $CH_3$ | H | $C_6H_{11}$ |
| $C_2H_5$ | H | $C_6H_{11}$ |
| $C_2H_5$ | H | Ph |
| $C_2H_5$ | H | 4-$(OC_2H_5)$—Ph |
| $C_2H_5$ | H | 4-$(COC_2H_5)$Ph |
| $ClCH_2CH_2$ | $CH_3$ | $CH_3$ |
| $ClCH_2CH_2$ | H | 4-$CH_3$Ph |
| n-$C_3H_7$ | H | n-$C_3H_7$ |
| i-$C_3H_7$ | H | Ph |
| $C_{12}H_{25}$ | $CH_3$ | $CH_3$ |
| $C_{18}H_{37}$ | $CH_3$ | $CH_3$ |
| —$CH_2CH=CH_2$ | H | —$CH_2CH=CH_2$ |
| —$CH_2CH=CH_2$ | H | Ph |
| $C_6H_{11}$ | $CH_3$ | $CH_3$ |
| $C_6H_{11}$ | H | Ph |
| Ph | $CH_3$ | $CH_3$ |
| Ph | H | Ph |
| Ph | H | n-$C_3H_7$ |
| Ph | H | n-$C_4H_9$ |
| Ph | H | 4-$(COC_2H_5)$Ph |

J. Med. Chem. 8, 781–784 (1965) describes the following compounds which are useful as hypoglycemic agents.

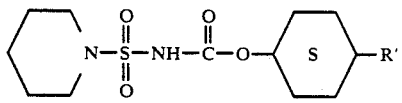

Tetrahedron Letters 24, (30) 3091–3094 (1983) describes the following compounds. No use is described for these compounds.

$XCH_2CH_2OCNH\underset{O}{\overset{O}{-S-}}NHR$

| X | R |
|---|---|
| Cl | Ph |
| Br | Ph |
| Cl | —$CH_2$—Ph |
| Cl | —$(C_2H_5)_2$ |
| Cl | $C_6H_{11}$ |
| Cl | —$(CH_2)_4 CH_3$ |

SUMMARY OF INVENTION

The present invention provides compounds of the following general Formula I, methods of using said compounds, pharmaceutical compositions and process for preparing the compounds of Formula I one to six carbon atoms, phenoxy, hydroxy, fluorine, chlorine, bromine, nitro, trifluoromethyl, —COOH, COOalkyl wherein alkyl has from one to four carbon atoms and is straight or branched, or —(CH$_2$)$_p$NR$_4$R$_5$ wherein p, R$_4$ and R$_5$ have the meanings defined above;

(d) —(CH$_2$)$_s$—Q wherein s is a number of from zero to three and Q is a 5- or 6-membered monocyclic or fused bicyclic heterocycle containing at least one to four nitrogen, oxygen or sulfur atoms in at least one ring member; or (e) a straight or branched hydrocarbon chain having from 1 to 20 carbon atoms and which is saturated or contains from one to three double bonds;

wherein each of R$_2$ and R$_3$ is
(a) hydrogen;
(b) the group

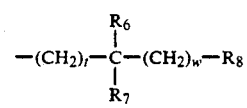

wherein t, w, R$_6$, R$_7$ and R$_8$ have the meanings defined above;

(c) a straight or branched hydrocarbon chain having from 1 to 20 carbon atoms and which is saturated or contains from one to three double bonds;

(d) an alkyl group having from one to six carbon atoms wherein the terminal carbon is substituted with hydroxy or —NR$_6$R$_7$ wherein R$_6$ and R$_7$ have the meanings defined hereinabove;

(e) —(CH$_2$)$_s$Q wherein s and Q have the meanings defined above;

(f) phenyl or phenyl substituted with from one to three substituents selected from
phenyl,
alkyl having from one to six carbon atoms and which is straight or branched,
alkoxy having from one to six carbon atoms and which is straight or branched,
phenoxy,
hydroxy,
fluorine,
chlorine,
bromine,
nitro,
trifluoromethyl,
—COOH,
—COOalkyl wherein the alkyl moiety has from one to four carbon atoms and is straight or branched, or
—(CH$_2$)$_p$NR$_4$R$_5$ wherein p, R$_4$, and R$_5$ have the meanings defined above; or (g) NR$_1$R$_2$ taken together form a monocyclic heterocyclic group selected from pyrrolidino, piperidino, morpholino, or piperazino, each of which is unsubstituted or substituted with one substituent selected from phenyl, straight or branched alkyl having from one to six carbon atoms; and pharmaceutically acceptable salts thereof; with the provisos:

(i) when each of R$_2$ and R$_3$ is the group

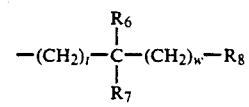

R$_7$ is hydrogen or alkyl having from one to six carbon atoms;

(ii) at least one of R$_1$, R$_2$, and R$_3$ is phenyl or substituted phenyl;

(iii) both R$_2$ and R$_3$ are not hydrogen at the same time;

(iv) when R$_1$ is phenyl disubstituted on the 2,6-positions or trisubstituted on the 2,4,6-positions with alkyl having from one to four carbon atoms, or when R$_1$ is phenyl disubstituted on the 2,6-positions with methoxy, neither of R$_2$ or R$_3$ is phenyl; and (v) the following compounds wherein Ph means phenyl are excluded:

| R$_1$ | R$_2$ | R$_3$ |
|---|---|---|
| C$_2$H$_5$ | H | 4-(OC$_2$H$_5$)Ph |
| C$_2$H$_5$ | H | 4-(—$\overset{\overset{O}{\|\|}}{C}$OC$_2$H$_5$)Ph |
| C$_2$H$_5$ | H | Ph |
| CH$_3$ | H | Ph |
| CH$_2$=CHCH$_2$ | H | Ph |
| C$_4$H$_9$ | H | Ph |
| Ph—CH$_2$— | H | C$_3$H$_7$ |
| 4(Cl)—Ph | H | —CH$_2$CH=CH$_2$ |
| i-C$_3$H$_7$ | H | Ph |
| Ph | CH$_3$ | CH$_3$ |
| Ph | H | Ph |
| Ph | H | n-C$_3$H$_7$ |
| Ph | H | n-C$_4$H$_9$ |
| Ph | H | 4-(—$\overset{\overset{O}{\|\|}}{C}$OC$_2$H$_5$)Ph |

The present invention also provides pharmaceutical compositions containing compounds of the following general Formula II and the method of treating hypercholesterolemia and atherosclerosis using the compounds of the following Formula II:

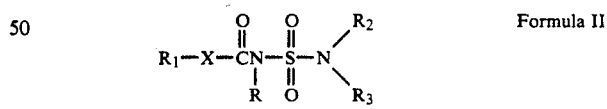

Formula II wherein X is sulfur or oxygen;
wherein R is hydrogen, a straight or branched alkyl having from 1 to 8 carbon atoms, or benzyl;
wherein R$_1$ is
(a) phenyl which is unsubstituted or is substituted with from one to three substituents selected from:
phenoxy,
hydroxy,
fluorine,
chlorine,
bromine,
nitro,
trifluoromethyl,
—COOH, —COOalkyl wherein alkyl has from one to four carbon atoms and which is straight or branched, —$(CH_2)_p NR_4 R_5$ wherein p is zero or one, and each of $R_4$ and $R_5$ is hydrogen or a straight or branched alkyl group having one to four carbon atoms;

(b) 1- or 2-naphthyl which is unsubstituted or substituted with one to three substituents selected from
phenyl,
alkyl having from one to six carbon atoms and which is straight or branched, alkoxy having from one to six carbon atoms and which is straight or branched,
hydroxy,
phenoxy,
fluorine,
chlorine,
bromine,
nitro,
trifluoromethyl,
—COOH,
—COOalkyl wherein alkyl has from one to four carbon atoms and is straight or branched,
—$(CH_2)_p NR_4 R_5$ wherein p, $R_4$, and $R_5$ have the meanings defined above;

(c) the group

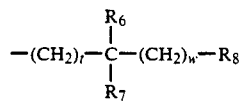

wherein t is zero or one to four; w is zero or one to four with the proviso that the sum of t and w is not greater than five; $R_6$ and $R_7$ are independently selected from hydrogen or alkyl having for one to six carbon atoms, or when $R_6$ is hydrogen, $R_7$ can be selected from the groups defined for $R_8$; and $R_8$ is phenyl or phenyl substituted with from one to three substituents selected from straight or branched alkyl having from one to six carbon atoms, straight or branched alkoxy having from one to six carbon atoms, phenoxy, hydroxy, fluorine, chlorine, bromine, nitro, trifluoromethyl, —COOH, COOalkyl wherein alkyl has from one to four carbon atoms and is straight or branched, or —$(CH_2)_p NR_4 R_5$ wherein p, $R_4$ and $R_5$ have the meanings defined above;

(d) —$(CH_2)_s$-Q wherein s is a number of from zero to three and Q is a 5- or 6-membered monocyclic or fused bicyclic heterocycle containing at least one to four nitrogen, oxygen or sulfur atoms in at least one ring member; or (e) a straight or branched hydrocarbon chain having from 1 to 20 carbon atoms and which is saturated or contains from one to three double bonds;
wherein each of $R_2$ and $R_3$ is
(a) hydrogen;
(b) the group

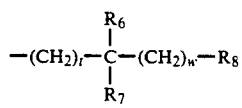

wherein t, w, $R_6$, $R_7$ and $R_8$ have the meanings defined above;

(c) a straight or branched hydrocarbon chain having from 1 to 20 carbon atoms and which is saturated or contains from one to three double bonds;

(d) an alkyl group having from one to six carbon atoms wherein the terminal carbon is substituted with hydroxy or —$NR_6 R_7$ wherein $R_6$ and $R_7$ have the meanings defined hereinabove;

(e) —$(CH_2)_s Q$ wherein s and Q have the meanings defined above;

(f) phenyl or phenyl substituted with from one to three substituents selected from
phenyl,
alkyl having from one to six carbon atoms and which is straight or branched,
alkoxy having from one to six carbon atoms and which is straight or branched,
phenoxy,
hydroxy,
fluorine,
chlorine,
bromine,
nitro,
trifluoromethyl,
—COOH,
—COOalkyl wherein the alkyl moiety has from one to four carbon atoms and is straight or branched, or
—$(CH_2)_p NR_4 R_5$ wherein p, $R_4$, and $R_5$ have the meanings defined above; or (g) $NR_1 R_2$ taken together form a monocycl heterocyclic group selected from pyrrolidino, piperidino, morpholino, or piperazino, each of which is unsubstituted or substituted with one substituent selected from phenyl, straight or branched alkyl having from one to six carbon atoms; and pharmaceutically acceptable salts thereof; with the provisos:

(i) when each of $R_2$ and $R_3$ is the group

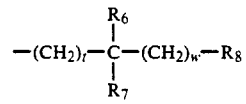

$R_7$ is hydrogen or alkyl having from one to six carbon atoms;

(ii) at least one of $R_1$, $R_2$, and $R_3$ is phenyl or substituted phenyl;

(iii) both $R_2$ and $R_3$ are not hydrogen at the same time.

DETAILED DESCRIPTION OF INVENTION

The compounds of the present invention provide a novel class of aminosulfonyl carbamates which are ACAT inhibitors rendering them useful in treating hypercholesterolemia and atherosclerosis.

Illustrative examples of straight or branched saturated hydrocarbon chains having from 1 to 20 carbon atoms include methyl, ethyl, n-propyl, isopropyl, n-butyl, iso-butyl, tert-butyl, n-pentyl, isopentyl, n-hexyl, n-heptyl, n-octyl, n-undecyl, n-dodecyl, n-hexadecyl, 2,2-dimethyldodecyl, 2-tetradecyl, and n-octadecyl groups.

Illustrative examples of straight or branched hydrocarbon chains having from 1 to 20 carbon atoms and having from 1 to 3 double bonds include ethenyl, 2-propenyl, 2-butenyl, 3-pentenyl, 2-octenyl, 5-nonenyl, 4-undecenyl, 5-heptadecenyl, 3-octadecenyl, 9- octadecenyl, 2,2-dimethyl-11-eicosenyl, 9,12-octadecadienyl, and hexadecenyl.

Straight or branched alkoxy groups having one to six carbon atoms include, for example, methoxy, ethoxy, n-propoxy, t-butoxy, and pentyloxy.

Straight or branched alkyl groups having from one to six carbon atoms include, for example, methyl, ethyl, n-propyl, isopropyl, n-butyl, n-pentyl, n-hexyl, and tert-butyl.

A 5- or 6-membered monocyclic or fused bicyclic heterocycle is a monocyclic or fused bicyclic aromatic ring containing at least one to four heteroatoms in at least one ring, such as nitrogen, oxygen, or sulfur or a combination thereof. Such a heterocyclic group includes, for example, thienyl, benzothienyl, furanyl, benzofuranyl, pyridyl, pyrimidinyl, pyridazinyl, pyrazinyl, pyrrolyl, pyrazolyl, isothiazolyl, thiazolyl, oxazolyl, isoxazolyl, triazolyl, tetrazolyl, imidazolyl, benzothiazolyl, indolyl, quinolinyl, isoquinolinyl, or N-oxides of heterocycle containing a nitrogen atom.

More specifically, such a heterocycle may be a 2- or 3-thienyl; 2- or 3-furanyl; 2-, or 3-, or 4-pyridyl or 2-, or 3-, or 4-pyridyl-N-oxide; 2-, 4-, or 5-pyrimidinyl; 3- or 4-pyridazinyl; 2-pyrazinyl; 2-pyrazinyl-N-oxide; 2- or 3-pyrrolyl; 3-, 4-, or 5-pyrazolyl; 2-, 4-, or 5-thiazolyl; 3-, 4-, or 5-isoxazolyl; 2-, 4-, or 5-oxazolyl; 3-, 4-, or 5-isothiazolyl; 5-tetrazolyl; 3- or 5-(1,2,4,-)triazolyl; 4- or 5-(1,2,3-)triazolyl; 2-, 4-, or 5-imidazolyl; 2-, 3-, 4-, 5-, 6-, or 7-indolyl; 2-, 3-, 4-, 5-, 6-, 7-, or 8-quinolinyl; 1-, 3-, 4-, 5-, 6-, 7-, or 8-isoquinolinyl; 2-, 4-, 5-, 6-, or 7-benzothiazolyl; or 2-, 3-, 4-, 5-, 6-, or 7-benzothienyl.

Preferred compounds of general Formulas I and II are those wherein one of $R_1$, $R_2$, and $R_3$ is phenyl disubstituted in the 2,6-positions. More preferably $R_1$ and $R_2$ are 2,6-disubstituted phenyl and $R_3$ is hydrogen. Compounds wherein $R_1$ is 2,6-disubstituted phenyl and $R_2$ and $R_3$ are a straight or branched hydrocarbon chain having from 1 to 20 carbon atoms, and more preferably, 6 to 18 carbon atoms, and which is saturated or contains from 1 to 3 double bonds are also preferred.

Pharmaceutically acceptable salts of the compounds of Formula I are also included as a part of the present invention.

The base salts may be generated from compounds of Formula I and Formula II by reaction of the latter with one equivalent of a suitable nontoxic, pharmaceutically acceptable base followed by evaporation of the solvent employed for the reaction and recrystallization of the salt, if required. The compounds of Formula I may be recovered from the base salt by reaction of the salt with an aqueous solution of a suitable acid such as hydrobromic, hydrochloric, or acetic acid, or by reaction with a suitable alkylating agent such as an alkyl halide, e.g., methyl iodide or benzyl bromide.

Suitable bases for forming base salts of the compounds of this invention include amines such as triethylamine or dibutylamine, or alkali metal bases and alkaline earth metal bases. Preferred alkali metal hydroxides and alkaline earth metal hydroxides as salt formers are the hydroxides of lithium, sodium, potassium, or calcium. The class of bases suitable for the formation of nontoxic, pharmaceutically acceptable salts is well known to practitioners of the pharmaceutical formulation arts. See, for example, Stephen N. Berge, et al, *J Pharm Sciences* 66:1-19 (1977).

Suitable acids for forming acid salts of the compounds of Formulas I and II containing a basic group include, but are not necessarily limited to acetic, benzoic, benzenesulfonic, tartaric, hydrobromic, hydrochloric, citric, fumaric, gluconic, glucuronic, glutamic, lactic, malic, maleic, methanesulfonic, pamoic, salicylic, stearic, succinic, sulfuric, and tartaric acids. The acid addition salts are formed by procedures well known in the art.

Certain compounds of the present invention may also exist in different stereoisomeric forms by virtue of the presence of asymmetric centers in the compound. The present invention contemplates all stereoisomers may be obtained, if desired, by methods known in the art as, for example, the separation of stereoisomers in chiral chromatographic columns.

Further, the compounds of this invention may exist in unsolvated as well as solvated forms with pharmaceutically acceptable solvents such as water, ethanol, and the like. In general, the solvated forms are considered equivalent to the unsolvated forms for the purposes of this invention.

As shown by the data presented below in Table 1, the compounds of the present invention are potent inhibitors of the enzyme acyl-CoA: cholesterol acyltransferase (ACAT), and are thus effective in inhibiting the esterification and transport of cholesterol across the intestinal cell wall. The compounds of the present invention are thus useful in pharmaceutical formulations for the treatment of hypercholesterolemia or atherosclerosis.

The ability of representative compounds of the present invention to inhibit ACAT was measured using an in vitro test more fully described in F. J. Field and R. G. Salone, *Biochemica et Biophysica* 712:557-570 (1982). The test assesses the ability of a test compound to inhibit the acylation of cholesterol by oleic acid by measuring the amount of radiolabeled cholesterol oleate formed from radiolabeled oleic acid in a tissue preparation containing rabbit intestinal microsomes.

The data appear in Table 1 where they are expressed as IC50 values; i. e., the concentration of test compound required to inhibit the activity of the enzyme by 50%.

TABLE 1

| Example No. | IAI $IC_{50}$ ($\mu M$) |
| --- | --- |
| 1 | >100 |
| 2 | 33 |
| 3 | 82 |
| 4 | 15 |
| 5 | 11.4 |
| 6 | 16.8 |
| 7 | 21.8 |
| 8 | 19 |
| 9 | 11 |
| 10 | 58 |
| 11 | 1.9 |
| 12 | 20 |
| 13 | 52 |
| 14 | 38 |
| 15 | 49 |
| 16 | 25.8 |
| 17 | 10.6 |
| 18 | 11.5 |
| 19 | 13.5 |
| 20 | 24.4 |
| 21 | 23.4 |
| 22 | 3.2 |
| 23 | 2.2 |
| 24 | 3.2 |
| 25 | 4.3 |
| 26 | 19.4 |
| 27 | 18.9 |
| 28 | 164 |
| 29 | 18 |

TABLE 1-continued

| Example No. | IAI IC$_{50}$ ($\mu$M) |
| --- | --- |
| 30 | 21 |
| 31 | 2.7 |
| 32 | 31 |
| 33 | 31 |
| 34 | 89 |
| 35 | 15 |
| 36 | 12 |
| 37 | 21 |
| 38 | 58 |
| 39 | 5.1 |
| 40 | 22 |
| 41 | 4.2 |
| 42 | 1.3 |
| 43 | 30.0 |
| 50 | >100 |
| 51 | >100 |
| 52 | 53 |
| 53 | >100 |
| 54 | 43 |
| 56 | >25 |
| 57 | 1.9 |
| 58 | 4.6 |

In one in vivo screen designated APCC, male Sprague-Dawley rats (200 to 225 g) were randomly divided into treatment groups and dosed at 4 PM with either vehicle (CMC/Tween) or suspensions of compounds in vehicle. The normal chow diet was then replaced with a high fat, high cholesterol diet with 0.5% cholic acid. The rats consumed this diet ad libitum during the night and were sacrificed at 8 AM to obtain blood samples for cholesterol analysis using standard procedures. Statistical differences between mean cholesterol values for the same vehicle were determined using analysis of variance followed by Fisher's least significant test. The results of this trial for representative compounds of the present invention appear in Table 2. The compounds were dosed at 30 mg/kg unless otherwise noted.

TABLE 2

| Compound of Example | % Change (mg/dl) |
| --- | --- |
| 1 | — |
| 2 | 0 |
| 3 | −55 |
| 4 | −77 |
| 5* | −35 |
| 6* | −57 |
| 7* | −32 |
| 8* | −26 |
| 9* | −3 |
| 10 | −67 |
| 11 | −57 |
| 12 | −43 |
| 13 | +8 |
| 14* | −55 |
| 15* | −29 |
| 16* | −65 |
| 17* | −46 |
| 18* | −42 |
| 19* | −56 |
| 20* | −54 |
| 21* | −33 |
| 22 | −4 |
| 23 | −42 |
| 24 | −19 |
| 25 | −40 |
| 26 | −52 |
| 27 | −29 |
| 28 | −13 |
| 29 | −55 |
| 30 | +2 |
| 31 | 0 |

TABLE 2-continued

| Compound of Example | % Change (mg/dl) |
| --- | --- |
| 32 | −10 |
| 33 | −22 |
| 34 | −4 |
| 35 | −76 |
| 36 | −70 |
| 37 | −58 |
| 38 | −70 |
| 39 | −60 |
| 40 | −60 |
| 41 | −62 |
| 42 | −74 |
| 43 | −8 |
| 50 | −14 |
| 51 | −11 |
| 52 | −53 |
| 53 | −21 |
| 54 | −77 |
| 56 | −39 |
| 57 | −66 |
| 58 | +4 |

*Indicates dosed at 50 mg/kg

In therapeutic use as agents for treating hypercholesterolemia or atherosclerosis, the compounds of Formula I or pharmaceutically acceptable salts thereof are administered to the patient at dosage levels of from 250 to 3000 mg per day. For a normal human adult of approximately 70 kg of body weight, this translates into a dosage of from 5 to 40 mg/kg of body weight per day. The specific dosages employed, however, may be varied depending upon the requirements of the patient, the severity of the condition being treated, and the activity of the compound being employed. The determination of optimum dosages for a particular situation is within the skill of the art.

For preparing the pharmaceutical compositions from the compounds of this invention, inert, pharmaceutically acceptable carriers can be either solid or liquid. Solid form preparations include powders, tablets, dispersible granules, capsules, and cachets.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active component is mixed with the carrier having the necessary binding properties in suitable proportions and compacted in the shape and size desired.

Powders and tablets preferably contain between about 5% to about 70% by weight of the active ingredient. Suitable carriers are magnesium dicarbonate, magnesium stearate, talc, lactose, sugar, pectin, dextrin, starch, tragacanth, methyl cellulose, sodium carboxymethyl cellulose, a low-melting wax, cocoa butter, and the like.

The term "preparation" is intended to include the formulation of the active compound with encapsulating material as a carrier providing a capsule in which the active component (with or without carriers) is surrounded by a carrier, which is thus in association with it. In a similar manner cachets are also included.

Tablets, powders, cachets, and capsules can be used as solid dosage forms suitable for oral administration.

Liquid form preparations include solutions, suspensions, or emulsions suitable for oral administration. Aqueous solutions for oral administration can be prepared by dissolving the active compound in water and adding suitable flavorants, coloring agents, stabilizers, and thickening agents as desired. Aqueous suspensions for oral use can be made by dispersing the finely divided active component in water together with a viscous material such as natural or synthetic gums, resins, methyl cellulose, sodium carboxymethylcellulose, and other suspending agents known to the pharmaceutical formulation art.

Preferably, the pharmaceutical preparation is in unit dosage form. In such form, the preparation is divided into unit doses containing appropriate quantities of the active component. The unit dosage form can be a packaged preparation containing discrete quantities of the preparation, for example, packeted tablets, capsules, and powders in vials or ampoules. The unit dosage form can also be a capsule, cachet, or tablet itself, or it can be the appropriate number of these packaged forms.

The compounds of general Formulas I and II are prepared as generally described in Chart I hereof.

An alcohol or thiol of the formula $R_1XH$ is reacted with chlorosulfonyl isocyanate in an inert organic solvent such as THF, $Et_2O$, $CH_2Cl_2$ at room temperature or preferably colder ($\leq 0°$ C.). The resulting chlorosulfonyl (thio) carbamate may precipitate out of solution or it can be triturated with a non polar solvent such as hexanes. The chlorosulfonyl (thio) carbamate can be isolated or it can be used as is and reacted with an amine of the formula $NHR_2R_3$ in an inert organic solvent such as those mentioned above at ambient temperature in the presence of an acid scavenger such as triethylamine. The oxysulfonyl (thio) carbamate thus formed can be converted to its base salt by reacting with an appropriate metal or amine base. The base salt can then be reacted with an appropriate alkylating agent such as methyl iodide or benzyl bromide.

The alcohols $R_1OH$, thiols, $R_1SH$, and amines $NHR_2R_3$ used in preparing the compounds of this invention are known in the art or are prepared by procedures generally known in the art.

The specific examples set forth below further illustrate the preparation of compounds of general Formula I and Formula II.

EXAMPLE 1

Methyl[[2,6-bis(1-methylethyl)phenylamino]sulfonyl]-carbamate

A solution of methyl(chlorosulfonyl) carbamate (5.0 g, 28.8 mmol) in 60 mL THF was added dropwise to a solution of 2,6-diisopropylaniline (5.11 g, 28.8 mmol) and excess triethylamine (~5 mL) in 100 mL THF at room temperature under an atmosphere of $N_2$. The mixture was stirred for 72 hrs, concentrated in vacuo and the residue was partitioned between 1N HCl and EtOAc. The organic layer was dried with $MgSO_4$, filtered and evaporated to give an orange oil which was triturated with 10% EtOAc/hexanes to give 5.93 g (65%) of an off-white solid, mp 152-155° C.

EXAMPLE 2

Dodecyl[[2,6-bis(1-methylethyl)phenyl]amino]sulfonyl]carbamate

A solution of dodecyl(chlorosulfonyl) carbamate (5.0 g, 15.2 mmol) in 70 mL THF was added dropwise to a solution of 2,6-diisopropylaniline (2.70 g, 15.2 mmol) and excess triethylamine (~5 mL) in 100 mL THF at room temperature under an atmosphere of $N_2$. The mixture was stirred for 16 hrs, concentrated in vacuo and partitioned between 1N HCl and EtOAc. The organic layer was dried with $MgSO_4$, filtered and concentrated to give an orange oil. Chromatography ($SiO_2$, 5% EtOAc/hex) gave 5.86 g (82%) of an off-white solid, mp 82°-84° C. (hexanes).

EXAMPLE 3

2,6-bis(1,1-dimethylethyl)-4-methoxyphenyl[[(2,2-diphenylethyl)amino]sulfonyl]carbamate A solution of 2,6-bis(1,1-dimethylethyl)-4-methoxyphenyl(chlorosulfonyl) carbamate (5.0 g, 13.2 mmol) in 80 mL THF was added dropwise to a solution of 2,2-diphenylethylamine (2.61 g, 13.2 mmol) and excess triethylamine (~3 mL) in 100 mL THF at room temperature under an atmosphere of $N_2$. The mixture was stirred for 72 hrs and then concentrated in vacuo. The residue was partitioned between 1N HCl and EtOAc. The organic layer was dried with $MgSO_4$, filtered and evaporated to give a clear oil which was triturated with hexanes to give 5.36 g (75%) of an off-white solid, mp 132°-138° C.

EXAMPLE 4

2,6-bis(1,1-dimethylethyl)-4-methoxy phenyl[[[2,6-bis(1-methylethyl)phenyl]amino]sulfonyl]-carbamate When in the general procedure of Example 3, an appropriate amount of 2,6-diisopropylaniline was substituted for 2,2-diphenylethylamine, the title compound was obtained, mp 155°-158° C.

EXAMPLE 5

2,6-bis(1,1-dimethylethyl)phenyl[[(diphenylmethyl)amino]sulfonyl]carbamate

A solution of 2,6-bis(1,1-dimethylethyl)phenyl (chlorosulfonyl) carbamate (2.85 g, 8.2 mmol) in 70 mL $Et_2O$ was added dropwise to a solution of diphenylmethylamine (1.50 g, 8.2 mmol) and triethylamine (1.25 mL, 9.0 mmol) in 80 mL $Et_2O$ at $-15°$ C. under an atmosphere of $N_2$. The mixture was warmed to room temperature and stirred for 6 hrs and then washed with 1N HCl and water. The organic layer was dried with $MgSO_4$, filtered and evaporated to give 3.60 g (89%) of an off-white solid, mp 162°-166° C.

EXAMPLE 6

2,6-bis(1,1-dimethylethyl)phenyl[[[2,6-bis(1-methylethyl)phenyl]amino]sulfonyl]carbamate When in the general procedure of Example 5, an appropriate amount of 2,6-diisopropylaniline was substituted for diphenylmethylamine, the title compound was obtained, mp 180°-181° C.

EXAMPLE 7

2,6-bis(1,1-dimethylethyl)phenyl[[(2,2-diphenylethyl)amino]sulfonyl]carbamate

When in the general procedure of Example 5, an appropriate amount of 2,2-diphenylethylamine was substituted for diphenylmethylamine, the title compound was obtained, mp 147°-150° C.

EXAMPLE 8

2,6-bis(1,1-dimethylethyl)phenyl[(phenylamino)sulfonyl]carbamate

When in general procedure of Example 5, an appropriate amount of aniline was substituted for diphenylmethylamine, the title compound was obtained, mp 169°-172° C.

EXAMPLE 9

2,6-bis(1,1-dimethylethyl)phenyl[[bis(phenylmethyl)amino]sulfonylcarbamate

When in general procedure of Example 5, an appropriate amount of dibenzylamine was substituted for diphenylamine, the title compound was obtained, mp 182°-183° C.

EXAMPLE 10

2,6-bis(1-methylethyl)phenyl[(diphenylamino)sulfonyl]carbamate

Solid NaH (0.68 g, 17.1 mmol) was added in portions to a solution of diphenylamine (2.41 g, 14.2 mmol) in 75 mL THF at room temperature under an atmosphere of $N_2$. The mixture was stirred for 16 hrs and then a solution of 2,6-bis(1-methylethyl)phenyl (chlorosulfonyl) carbamate (5.0 g, 15.6 mmol) in 50 mL THF was added dropwise. The reaction mixture was stirred for an additional 4 hrs and then quenched with 10 mL 1N HCl, and partitioned between 1N HCl and EtOAc. The organic layer was dried with $MgSO_4$, filtered, and evaporated to give a green oil which was triturated and recrystallized from hexane to give 3.21 g (50%) of the title compound as an off-white solid, mp 149°-151° C.

EXAMPLE 11

Synthesis of 2,6-Bis(1-methylethyl)phenyl[(dibutylamino)sulfonyl]carbamate

A solution of 2,6-bis(1-methylethyl)phenyl(chlorosulfonyl)carbamate (5.0 g, 15.66 mmoles) in 75 mL THF was added dropwise to a solution of di-n-butylamine (1.84 g, 14.2 mmoles) and excess triethylamine (~2 mL) in 75 mL THF. This was then stirred for 16 hours and then partitioned between 1N HCl and EtOAc. The organic layer was dried with $MgSO_4$, filtered, and evaporated to give a pale orange oil Chromatography ($SiO_2$, 5% EtOAc/hexane) gave 1.64 g (25%) of the title compound as a white solid, mp 94°-97° C.

EXAMPLE 12

Synthesis of 2,6-Bis(1-methylethyl)phenyl[[bis(phenylmethyl)amino]sulfonyl]carbamate When in the general procedure of Example 11, an appropriate amount of dibenzylamine was substituted for di-n-butylamine, the title compound was obtained, mp 143°-146° C.

EXAMPLE 13

Synthesis of 2,6-Bis(1-methylethyl)phenyl(1H-benzimidazol-2-ylamino)sulfonyl]carbamate When in the general procedure of Example 11, an appropriate amount of 2-aminobenzimidazole was substituted for di-n-butylamine, the title compound was obtained, mp 159°-162° C.

EXAMPLE 14

Synthesis of 2,6-Bis(1-methylethyl)phenyl[(phenylamino)sulfonyl]carbamate

When in the general procedure of Example 11, an appropriate amount of aniline was substituted for di-n-butylamine, the title compound was obtained, mp 165°-168° C.

EXAMPLE 15

Synthesis of 2,6-Bis(1-methylethyl)phenyl[2,2-diphenylethyl)amino]sulfonyl]carbamate When in the general procedure of Example 11, an appropriate amount of 2,2-diphenylethylamine was substituted for di-n-butylamine, the title compound was obtained, mp 103°-105° C.

EXAMPLE 16

Synthesis of 2,6-Bis(1-methylethyl)phenyl[[2,6-bis(1methylethyl)phenyl]amino]sulfonyl]carbamate When in the general procedure of Example 11, an appropriate amount of 2,6-diisopropylaniline was substituted for di-n-butylamine, the title compound was obtained, mp 172°-174° C.

EXAMPLE 17

Synthesis of 2,6-Bis(1-methylethyl)phenyl[(diphenylmethyl)amino]sulfonyl]carbamate When in the general procedure of Example 11, an appropriate amount of diphenylmethylamine was substituted for di-n-butylamine, the title compound was obtained, mp 185°-187° C.

EXAMPLE 18

Synthesis of 2,6-Bis(1,1-dimethylethyl)-4-methylphenyl[[(diphenylmethyl)amino]sulfonyl carbamate A solution of 2,6-bis(1,1-dimethylethyl)-4-methylphenyl(chlorosulfonyl)carbamate (2.96 g, 8.2 mmoles) in 70 mL $Et_2O$ was added dropwise to a solution of diphenylmethylamine (1.5 g, 8.2 mmoles) and 1.25 mL (10.0 mmoles) of triethylamine in 80 mL $Et_2O$ at −15° C. under an atmosphere of $N_2$. The mixture was allowed to warm to room temperature over 2 hours and then washed with 1N HCl and $H_2O$. The $Et_2O$ layer was dried with $MgSO_4$, filtered, and evaporated to give a pale yellow foam which was triturated with hexanes to give a white solid, mp 150°-152° C.

EXAMPLE 19

Synthesis of 2,6-Bis(1,1-dimethylethyl)-4-methylphenyl[[[bis(2,6-bis(1-methylethyl)phenyl]amino]sulfonyl]carbamate When in the procedure of Example 18, an appropriate amount of 2,6-diisopropylaniline was substituted for diphenylmethylamine, the title compound was obtained, mp 176°-178° C.

EXAMPLE 20

Synthesis of
2,6-Bis(1,1-dimethylethyl)-4-methylphenyl[[[(2,2-diphenylethyl)amino]sulfonyl]carbamate When in the general procedure of Example 18, an appropriate amount of 2,2-diphenylethylamine was substituted for diphenylmethylamine, the title compound was obtained. mp 139°–141° C.

EXAMPLE 21

Synthesis of
2,6-Bis(1,1-dimethylethyl)-4-methylphenyl[(-phenylamino)sulfonyl]carbamate When in the general procedure of Example 18, an appropriate amount of aniline was substituted for diphenylmethylamine, the title compound was obtained, mp 186°–188° C.

EXAMPLE 22

Synthesis of
2,6-Bis(1,1-dimethylethyl)-4-methylphenyl[-(dibutylamino)sulfonyl]carbamate When in the general procedure of Example 18, an appropriate amount of di-n-butylamine was substituted for diphenylmethylamine, the title compound was obtained, mp 134°–135° C.

EXAMPLE 23

Synthesis of
2,6-Bis(1,1-dimethylethyl)-4-methylphenyl[(dipentylamino)sulfonyl]carbamate When in the general procedure of Example 18, an appropriate amount of di-n-pentylamine was substituted for diphenylmethylamine, the title compound was obtained, mp 107°–108° C.

EXAMPLE 24

Synthesis of
2,6-Bis(1,1-dimethylethyl)-4-methylphenyl[[bis(1-methylethyl)amino]sulfonyl]carbamate When in the general procedure of Example 18, an appropriate amount of diisopropylamine was substituted for diphenylmethylamine, the title compound was obtained, mp 198°–199° C.

EXAMPLE 25

Synthesis of
2,6-Bis(1,1-dimethylethyl)-4-methylphenyl(dihexylamino)sulfonyl]carbamate When in the general procedure of Example 18, an appropriate amount of di-n-hexylamine was substituted for diphenylmethylamine, the title compound was obtained, mp 66°–68° C.

EXAMPLE 26

Synthesis of
2,6-Bis(1,1-dimethylethyl)-4-methylphenyl[(hexylamino)sulfonyl]carbamate When in the general procedure of Example 18, an appropriate amount of hexylamine was substituted for diphenylmethylamine, the title compound was obtained, mp 123°–128° C.

EXAMPLE 27

Synthesis of
2,6-Bis(1,1-dimethylethyl)-4-methylphenyl[[methyl(2-phenylethyl)amino]sulfonyl]carbamate When in the general procedure of Example 18, an appropriate amount of N-methyl-2-phenylethylamine was substituted for diphenylmethylamine, the title compound was obtained, mp 140°–142° C.

EXAMPLE 28

Synthesis of
2,6-Bis(1,1-dimethylethyl)-4-methylphenyl[[[bis-3-(dimethylamino)propyl]amino]sulfonyl]carbamate When in the general procedure of Example 18, an appropriate amount of bis-3-(dimethylamino)propyl amine was substituted for diphenylmethylamine, the title compound was obtained. $^1$H NMR (CDCl$_3$) δ 8.05 (bs, 1H), 7.05 (s, 2H), 3.29 (m, 4H), 2.87 (m, 4H), 2.56 (s, 12H), 2.29 (s, 3H), 1.91 (m, 4H), 1.37 (s, 18H) ppm.

EXAMPLE 29

Synthesis of
2,6-Bis(1,1-dimethylethyl)-4-methylphenyl[(methyl octyl amino)sulfonyl]carbamate When in the general procedure of Example 18, an appropriate amount of N-methyl octylamine was substituted for diphenylmethylamine, the title compound was obtained, mp 65°–68° C.

EXAMPLE 30

Synthesis of
2,6-Bis(1,1-dimethylethyl)-4-methyl[[bis[(tetrahydro-2-furanyl)methyl]amino]sulfonyl]carbamate When in the general procedure of Example 18, an appropriate amount of bis-[(tetrahydro-2-furanyl)-methyl] amine was substituted for diphenylmethylamine, the title compound was obtained, mp 108°–111° C.

EXAMPLE 31

Synthesis of
2,6-Bis(1,1-dimethylethyl)-4-methylphenyl[(dioctylamino)sulfonyl]carbamate When in the general procedure of Example 18, an appropriate amount of di-n-octylamine was substituted for diphenylmethylamine, the title compound was obtained, mp 53°–55° C.

EXAMPLE 32

Synthesis of
2,6-Bis(1,1-dimethylethyl)-4-methylphenyl[[[methyl 2-(2-pyridinyl)ethyl]amino]sulfonyl]carbamate, hydrochloride salt A solution of 2,6-bis(1,1-dimethylethyl)-4-methylphenyl(chlorosulfonyl)carbamate (5.0 g, 13.8 mmoles) in 70 mL THF was added dropwise to a solution of 2-(β-methylaminoethyl)pyridine (1.88 g, 13.8 mmoles) and excess triethylamine (~2 mL) in 80 mL THF at room temperature under an atmosphere of N$_2$. The solution was stirred for 16 hours and then concentrated in vacuo. The residue was partitioned between 1N HCl and EtOAc, the EtOAc layer dried with MgSO$_4$, filtered, and evaporated to give a white solid which was then triturated with hexanes to give 5.00 g of the title compound, mp 178°–181° C.

EXAMPLE 33

Synthesis of 2,6-Bis(1,1-dimethylethyl)-4-methylphenyl[[[methyl 2-(2-pyridinyl)ethyl]amino]sulfonyl]carbamate, sodium salt Excess 1N NaOH (30 mL) was added to a suspension of 2,6-bis(1,1-dimethylethyl)-4-methylphenyl[[[methyl 2-(2-pyridinyl)ethyl]amino]sulfonyl]carbamate hydrochloride (2.75 g, 5.5 mmoles) in 50 mL EtOAc. The mixture was stirred for 16 hours, the organic layer separated, dried with MgSO$_4$, filtered, and evaporated to give a clear oil which was triturated with hexanes to give the title compound as a white solid, mp 133°–136° C.

EXAMPLE 34

Synthesis of 2,6-Bis(1,1-dimethylethyl)-4-methylphenyl[(dodecylamino)sulfonyl]carbamate When in the general procedure of Example 18, an appropriate amount of di-n-decylamine was substituted for diphenylmethylamine, the title compound was obtained as a waxy white solid, mp 63°–65° C.

EXAMPLE 35

Synthesis of 2,6-Bis(1-methylethyl)phenyl[bis(1methylethyl)amino]sulfonyl]carbamate When in the general procedure of Example 11, an appropriate amount of diisopropylamine was substituted for di-n-butylamine, the title compound was obtained, mp 126°–131° C.

EXAMPLE 36

Synthesis of 2,6-Bis(1-methylethyl)phenyl[(1methylethyl)phenylmethyl)amino]sulfonyl]carbamate When in the general procedure of Example 11, an appropriate amount of N-isopropyl benzylamine was substituted for di-n-butylamine, the title compound was obtained, mp 156°–159° C.

EXAMPLE 37

Synthesis of 2,6-Bis(1-methylethyl)phenyl(hexylamino)sulfonyl]carbamate

When in the general procedure of Example 11, an appropriate amount of n-hexylamine was substituted for di-n-butylamine, the title compound was obtained, mp 105°–106.5° C.

EXAMPLE 38

Synthesis of 2,6-Bis(1-methylethyl)phenyl[(dioctylamino)sulfonyl]carbamate

When in the general procedure of Example 11, an appropriate amount of di-n-octylamine was substituted for di-n-butylamine, the title compound was obtained, mp 64°–67° C.

EXAMPLE 39

Synthesis of 2,6-Bis(1-methylethyl)phenyl[[cyclohexyl(1-methylethyl)amino]sulfonyl]carbamate When in the general procedure of Example 11, an appropriate amount of N-isopropylcyclohexylamine was substituted for di-n-butylamine, the title compound was obtained, mp 133°–135° C.

EXAMPLE 40

Synthesis of 2,6-Bis(1-methylethyl)phenyl(methyloctylamino)sulfonyl]carbamate

When in the general procedure of Example 11, an appropriate amount of N-methyloctylamine was substituted for di-n-butylamine, the title compound was obtained, mp 32°–35° C.

EXAMPLE 41

Synthesis of 2,6-Bis(1-methylethyl)phenyl[(dihexylamino)sulfonyl]carbamate

When in the general procedure of Example 11, an appropriate amount of di-n-hexylamine was substituted for di-n-butylamine, the title compound was obtained, mp 57°–61° C.

EXAMPLE 42

Synthesis of 2,6-Bis(1-methylethyl)phenyl[(dipentylamino)sulfonyl]carbamate

When in the general procedure of Example 11, an appropriate amount of di-n-pentylamine was substituted for di-n-butylamine, the title compound was obtained, mp 69°–70° C.

EXAMPLE 43

Synthesis of Dodecyl[[(2,4,6-trimethoxyphenyl)amino]sulfonyl]carbamate

When in the general procedure of Example 2, an appropriate amount of 2,4,6-trimethoxyaniline was substituted for 2,6-diisopropylaniline, the title compound was obtained, mp 133°–136° C.

The following Example 44 through 49 teach the preparation of intermediates useful in preparing final products of the present invention.

EXAMPLE 44

Synthesis of Methyl(chlorosulfonyl)carbamate (Ref: Org. Synth. 56 40 (1977))

A solution of methanol (10.2 mL, 252 mmoles) in 15 mL toluene was added dropwise to a solution of chlorosulfonyl isocyanate (22.0 mL, 252 mmoles) in 75 mL toluene at 0° C. The cooling bath was removed and stirred for one-half hour at room temperature. This was then cooled to 0° C. and 65 mL ice cold hexanes was added. The white precipitate was collected by filtration and washed 2 times with a small amount of cold hexane to give 33.0 g of a white solid, mp 72°–74° C.

EXAMPLE 45

Synthesis of Dodecyl(chlorosulfonyl)carbamate (Ref: R. Graf, Chem. Ber. 96 56 (1963))

A solution of n-dodecyl alcohol (107 g. 52.4 mmoles) in 100 mL $Et_2O$ was added dropwise to a solution of chlorosulfonyl isocyanate (5.0 mL, 57.4 mmoles) in 100 mL $Et_2O$ at $-15°$ C. under an atmosphere of $N_2$. The resulting mixture was stirred for 2 hours and concentrated in vacuo. The residue was triturated with cold hexanes to give a white solid which was collected by filtration to give 19.12 g of a white solid, mp 62°–63° C.

EXAMPLE 46

Synthesis of 2,6-Bis(1-methylethyl)phenyl(chlorosulfonyl)carbamate (Ref: Phos & Sulf 19 167 (1984))

A solution of 2,6-diisopropylphenol (37.1 mL, 0.2 moles) in 200 mL $Et_2O$ was added dropwise to a solution of chlorosulfonyl isocyanate (17.4 mL, 0.2 moles)) in 200 mL $Et_2O$ at $-15°$ C. This was then stored at $-15°$ C. under an atmosphere of $N_2$ for 16 hours. Concentration gave an orange oil which was triturated with hexanes and quickly collected by filtration to give 55.64 g (87%) of product as a white solid.

EXAMPLE 47

Synthesis of 2,6-Bis(1,1-dimethylethyl)phenyl(chlorosulfonyl)carbamate (Ref: Phos & Sulf 19 167 (1984))

A solution of 2,6-di-t-butylphenol (20.63 g, 0.1 mol) in 100 mL $Et_2O$ was added dropwise to a solution of chlorosulfonyl isocyanate (8.7 mL, 0.1 moles) in 100 mL $Et_2O$ at $-15°$ C. (acetone/ice bath) under an atmosphere of $N_2$. This was stirred for 1 hour and then concentrated in vacuo to leave a thick gel which was triturated with hexanes and filtered to give 28.60 g (82%) of the title compound as a white solid, mp 135°–137° C.

EXAMPLE 48

Synthesis of 2,6-Bis(1,1-dimethylethyl)-4-methylphenyl(chlorosulfonyl)carbamate (Ref: phos & Sulf 19 167 (1984))

A solution of 2,6-di-t-butyl-4-methylphenol (22.04 g, 0.1 moles) in 100 mL $Et_2O$ was added dropwise to a solution of chlorosulfonyl isocyanate (8.7 mL, 0.1 moles) in 100 mL $Et_2O$ at $-15°$ C. under an atmosphere of $N_2$. This was stirred for 2 hours, concentrated and trituration of the resulting gel with hexanes gave 26.82 g (74%) of the title compound as a white solid.

EXAMPLE 49

Synthesis of 2,6-Bis(1,1-dimethylethyl)-4-methoxyphenyl(chlorosulfonyl)carbamate A solution of 3,5-di-t-butyl-4-hydroxyanisole (30.0 g, 0.127 moles) in 200 mL $Et_2O$ was added dropwise to a solution of chlorosulfonyl isocyanate (12.2 mL, 0.14 moles) in 250 mL $Et_2O$ at $-15°$ C. under an atmosphere of $N_2$. This was stirred for 1 hour and then concentrated in vacuo to give 41.0 g of product as a thick gel which was used without further purification.

The examples set forth hereinbelow further illustrate the preparation of final products of the compounds of the present invention.

When in the procedure of Example 11 an appropriate amount of the amine listed below was substituted for di-n-butylamine the respective product listed below was obtained:

| Example No. | Amine | Product |
|---|---|---|
| 50 | Morpholine | 2,6—Bis(1-methylethyl)-phenyl ester(4-morpholinylsulfonyl)-carbamic acid; $^1H$ NMR ($CDCl_3$) δ 7.9 (bs, 1H), 7.1(m, 3H), 3.7(t, 4H), 3.5(5, 4H), 3.0(m, 2H), 1.2 (d, 12H)ppm. |
| 51 | Piperidine | 2,6-Bis(1-methylethyl)-phenyl ester(1-piperidinylsulfonyl)-carbamic acid; $^1H$ NMR ($CDCl_3$) δ 8.1 (bs, 1H), 7.1(m, 3H), 3.4(t, 4H), 3.0(m, 2H), 1.7(m, 4H), 1.6 (m, 2H), 1.2(d, 12H)ppm |
| 52 | Pyrrolidine | 2,6-Bis(1-methylethyl)-phenyl ester(1-pyrrolidinylsulfonyl)-carbamic acid; $^1H$ NMR ($CDCl_3$) δ 7.8 (bs, 1H), 7.1(m, 3H), 3.6(t, 4H), 3.0(m, 2H), 1.9(t, 4H), 1.2 (d, 12H)ppm. |
| 53 | 4-Methylpiperazine | 2,6-Bis(1-methylethyl)-phenyl ester, monohydrochloride[(4-methyl-1-piperazinyl)-sulfonyl]carbamic acid; 1H NMR (DMSO $D_6$) δ 8.0 (s, 1H), 7.0(d, 3H), 3.3(m, 2H), 3.1(bs, 4H), 2.8(bs, 4H), 2.5 (s, 3H), 1.1(d, 12H)ppm. |
| 54 | 2,3-Dihydroindole | 2,6-Bis(1-methylethyl)-phenyl ester[(2,3-dihydro-1H-indol-1-yl)sulfonyl[carbamic acid; $^1H$ NMR ($CDCl_3$) δ 8.0(bs, 1H), 7.4(d, 1H), 7.2(m, 3H), 7.1 (m, 3H), 4.4(t, 2H), 3.1(t, 2H), 2.5(m, 2H), 1.0(d, 12H)ppm. |

EXAMPLE 55

Synthesis of [1,1':3',1''-terphenyl]-2,-yl(chlorosulfonyl)carbamate

A solution of 2,6-diphenyl phenol (25.0 g, 101 mmol) in 250 mL ethyl ether was added dropwise to a solution of chlorosulfonyl isocyanate (9.7 mL, 112 μmol) in 100 mL hexane at $-15°$ C. under an atmosphere of nitrogen. The resulting white suspension was allowed to warm to room temperature over 2 hours. Concentrated in vacuo and triturated with ice cold hexane. Vacuum filtration afforded the title compound as a white solid, mp 159°–162° C.

EXAMPLE 56

Synthesis of 1,1, 3',1''-terphenyl]-2,-yl[[2,6-bis(1methylethyl)phenyl-]amino]sulfonyl]carbamate A solution of [1,1':3',1''-terphenyl]-2,-yl(chlorosulfonyl)carbamate (5.0 g, 12.9 mmol) in 75 mL tetrahydrofuran was added dropwise to a solution of 2,6-diisopropyl aniline (2.29 g, 12.9 mmol) and triethylamine (1.3 g, 12.9 mmol) in 100 mL tetrahydrofuran at $-15°$ C. under an atmosphere of nitrogen. The resulting mixture was warmed to room temperature and stirred for 16 hours. Concentrated in vacuo and partitioned the residue between water and ethyl acetate. Dried the organic layer over MgSO$_4$ and evaporated to give an off-white solid. Chromatography on silica gel gave the title compound, mp 166°–168° C.

EXAMPLE 57

Synthesis of 2,6-bis(1-methylethyl)phenyl[(dibutylamino)sulfonyl]-carbamate monosodium salt A solution of the 2,6-bis(1-methylethyl)phenyl[-(dibutylamino)sulfonyl]carbamate (5.5 g, 13.3 mmol) in 75 mL tetrahydrofuran was added dropwise to a suspension of sodium hydride (0.4 g, 80% dispersion in mineral oil, 13.3 mmol) in 50 mL tetrahydrofuran at 0° C. under an atmosphere of nitrogen. Stirred for 3 hours, gradually warming to room temperature. Concentrated in vacuo and triturated with hexanes to give the title compound, mp 162°–166° C.

EXAMPLE 58

Synthesis of 2,6-bis(1,1-dimethylethyl)phenyl[[(diphenylmethyl-)amino]sulfonyl]methyl carbamate 1,8-Diazabicyclo[5.4.0]undec-7-ene (1.0 mL, 6.7 mmol) was added in one portion to a solution of 2,6-bis(1,1-dimethylethyl)phenyl[[(diphenylmethyl)amino]-sulfonyl]carbamate (3.0 g, 6.1 mmol) and methyl iodide (0.95 g, 6.7 mmol) in 50 mL acetonitrile at room temperature and the resulting mixture was stirred for 16 hours. Partitioned between 1N HCl and ethyl acetate. Dried the organic layer over MgSO$_4$, filtered, and evaporated to give an orange oil. Chromatography on silica gel gave the title compound, mp 175°–178° C.

CHART I

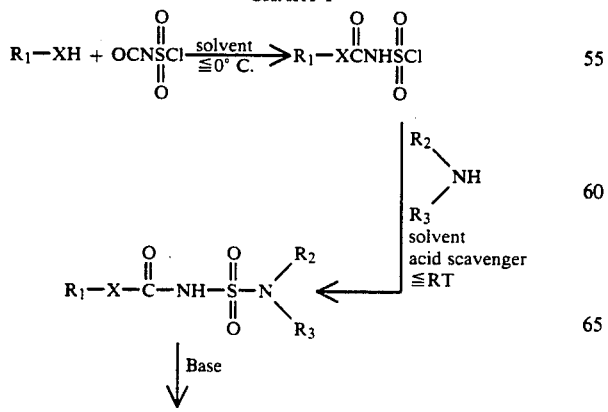

-continued
CHART I

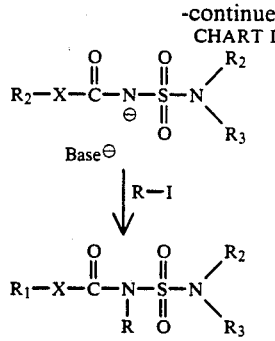

We claim:
1. A compound of the formula

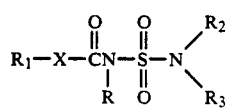

Formula I wherein X=oxygen or sulfur; R is hydrogen, a straight or branched alkyl group having from 1 to 8 carbon atoms, or benzyl;

wherein R$_1$ is (a) phenyl substituted with from one to three substituents selected from:
phenyl,
alkyl having from one to six carbon atoms and which is straight or branched,
alkoxy having from one to six carbon atoms and which is straight or branched,
phenoxy,
hydroxy,
fluorine,
bromine,
nitro,
trifluoromethyl,
—COOH,
—COOalkyl wherein alkyl has from one to four carbon atoms and which is straight or branched,
—(CH$_2$)$_p$NR$_4$R$_5$ wherein p is zero or one, and each of R$_4$ and R$_5$ is hydrogen or a straight or branched alkyl group having one to four carbon atoms;

(b) 1- or 2-naphthyl which is unsubstituted or substituted with one to three substituents selected from
phenyl,
alkyl having from one to six carbon atoms and which is straight or branched,
alkoxy having from one to six carbon atoms and which is straight or branched,
phenoxy,
hydroxy,
fluorine,
chlorine,
bromine,
nitro,
trifluoromethyl,
—COOH,
—COOalkyl wherein alkyl has from one to four carbon atoms and is straight or branched,
—(CH$_2$)$_p$NR$_4$R$_5$ wherein p, R$_4$, and R$_5$ have the meanings defined above; or (c) —(CH$_2$)$_2$—Q wherein s is a number of form zero to three and Q is a 4- or 6-membered monocyclic or fused bicyclic heterocycle containing at least one to four nitrogen, oxygen or sulfur atoms in at least one ring member;

wherein each of R$_2$ and R$_3$ is
(a) hydrogen;
(b) the group

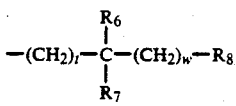

wherein t is zero or one to four; w is zero or one to four with the proviso that the sum of t and w is not greater than five; R$_6$ and R$_7$ are independently selected from hydrogen or alkyl having for one to six carbon atoms, or when R$_6$ is hydrogen, R$_7$ can be selected from the groups defined for R$_8$; and R$_8$ is phenyl or phenyl substituted with from one to three substituents selected from straight or branched alkyl having from one to six carbon atoms, straight or branched alkoxy having from one to six carbon atoms, phenoxy, hydroxy, fluorine, chlorine, bromine, nitro, trifluoromethyl, —COOH, COOalkyl wherein alkyl has from one to four carbon atoms and is straight or branched, or —(CH$_2$)$_p$NR$_4$R$_5$ wherein p, R$_4$ and R$_5$ have the meanings defined above;

(c) a straight or branched hydrocarbon chain having from 1 to 20 carbon atoms and which is saturated or contains from one to three double bonds;

(d) an alkyl group having from one to six carbon atoms wherein the terminal carbon is substituted with hydroxy or —NR$_6$R$_7$ wherein R$_6$ and R$_7$ have the meanings defined hereinabove;

(e) —(CH$_2$)$_s$Q wherein s and Q have the meanings defined above;

(f) phenyl or phenyl substituted with from one to three substituents selected from phenyl,
alkyl having form one to six carbon atoms and which is straight or branched,
alkoxy having from one to six carbon atoms and which is straight or branched,
phenoxy,
hydroxy,
fluorine,
chlorine,
bromine,
nitro,
trifluoromethyl,
—COOH,
—COOalkyl wherein the alkyl moiety has from one to four carbon atoms and is straight or branched, or
—(CH$_2$)$_p$NR$_4$R$_5$ wherein p, R$_4$, and R$_5$ have the meanings defined above; or (g) NR$_2$R$_3$ taken together form a monocyclic heterocyclic group selected form pyrrolidino, piperidino, morpholino, or piperazino, each of which is unsubstituted or substituted with one substituent selected from phenyl, straight or branched alkyl having from one to six carbon atoms; and pharmaceutically acceptable salts thereof; with the provisos:

(i) when each of R$_2$ and R$_3$ is the group

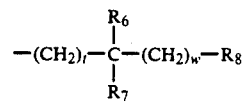

R$_7$ is hydrogen or alkyl having from one to six carbon atoms;

(ii) at least one of R$_1$,R$_2$, and R$_3$ is phenyl or substituted phenyl;

(iii) both R$_2$ and R$_3$ are not hydrogen at the same time;

(iv) when R$_1$ is phenyl disubstituted on the 2,6-positions with alkyl having form one to four carbon atoms or with methoxy, or trisubstituted on the 2,4,6-positions with alkyl having from one t four carbon atoms, neither of R$_2$ or R$_3$ is phenyl; and (v) the following compound wherein Ph means phenyl is excluded:

2. A compound of claim 1 wherein R$_1$ is disubstituted in the 2,6-positions.

3. A compound of claim 2 wherein R$_2$ is substituted or unsubstituted phenyl.

4. A compound of claim 3 wherein R$_2$ is phenyl disubstituted in the 2,6-positions.

5. A compound of claim 4 wherein R$_3$ is hydrogen.

6. A compound of claim 1 which is:

2,6-Bis(1,1-dimethylethyl)-4-methoxyphenyl[[(2,2-diphenylethyl)amino]sulfonyl]carbamate, 2,6-Bis(1,1-dimethylethyl)-4-methoxy phenyl [[[2,6-bis(1-methylethyl)phenyl]amino]sulfonyl]carbamate, 2,6-Bis(1,1-dimethylethyl)phenyl[[(diphenylmethyl)amino]sulfonyl]carbamate, 2,6-Bis(1,1-dimethylethyl)phenyl [[[2,6-bis(1-methylethyl)phenyl]amino]sulfonyl]carbamate, 2,6-Bis(1,1-dimethylethyl)-phenyl [[(2,2-diphenylethyl)amino]sulfonyl]carbamate, 2,6-Bis(1,1-dimethylethyl)phenyl [[bis(phenylmethyl)amino]sulfonyl]carbamate, 2,6-bis(1-methylethyl)phenyl[(diphenylamino)sulfonyl]carbamate, 2,6-Bis(1-methylethyl)phenyl[(dibutylamino)sulfonyl]carbamate, 2,6-Bis(1-methylethyl)phenyl[[bis(phenylmethyl)amino]sulfonyl]carbamate, 2,6-Bis(1-methylethyl)phenyl[(1H-benzimidazol-2-ylamino)sulfonyl]carbamate, 2,6-Bis(1-methylethyl)phenyl[[2,2-diphenylethyl)amino]sulfonyl]carbamate, 2,6-Bis(1-methylethyl)phenyl[[[2,6-bis(1-methylethyl)phenyl]amino]sulfonyl]carbamate, 2,6-Bis(1-methylethyl)phenyl[[(diphenylmethyl)amino]sulfonyl]carbamate, 2,6-Bis(1,1-dimethylethyl)-4-methylphenyl[κ(diphenylmethyl)amino[sulfonyl]carbamate, 2,6-Bis(1,1-dimethylethyl)-4-methylphenyl[[[bis(2,6-bis(1-methylethyl)phenyl]amino]sulfonyl]carbamate, 2,6-Bis(1,1-dimethylethyl)-4-methylphenyl[[(2,2-diphenylethyl)amino]sulfonyl]carbamate, 2,6-Bis(1,1-dimethylethyl)-4-methylphenyl[-(dibutylamino)sulfonyl]carbamate, 2,6-Bis(1,1-dimethylethyl)4-methylphenyl[(dipentylamino)sulfonyl]carbamate, 2,6-Bis(1,1-dimethylethyl)-4methylphenyl[[bis(1-methylethyl)amino]sulfonyl]carbamate, 2,6-Bis(1,1-dimethylethyl)-4-methylphenyl[(dihexylamino)sulfonyl]carbamate,
2,6-Bis(1,1-dimethylethyl)-4-methylphenyl[(hexylamino)sulfonyl]carbamate,
2,6-Bis(1,1-dimethylethyl)-4-methylphenyl[[methyl(2-phenylethyl)amino]sulfonyl]carbamate,
2,6-Bis(1,1-dimethylethyl)-4-methylphenyl[κ[bis-3-(dimethylamino)propyl]amino]sulfonyl]carbamate,
2,6-Bis(1,1-dimethylethyl)-4-methylphenyl[(methyl octyl amino)sulfonyl]carbamate,
2,6-Bis(1,1-dimethylethyl)-4-methyl[[bis[(tetrahydro-2-furanyl)methyl]amino]sulfonyl]carbamate,
2,6-Bis(1,1-dimethylethyl)-4-methylphenyl[(dioctylamino)sulfonyl]carbamate,
2,6-Bis(1,1-dimethylethyl)-4-methylphenyl[[[methyl 2-(2-pyridinyl)ethyl]amino]sulfonyl]carbamate, hydrochloride salt,
2,6-Bis(1,1-dimethylethyl)-4-methylphenyl[[[methyl 2-(2-pyridinyl)ethyl]amino]sulfonyl]carbamate, sodium salt,
2,6-Bis(1,1-dimethylethyl)-4-methylphenyl[(dodecylamino)sulfonyl]carbamate,
2,6-Bis(1-methylethyl)phenyl[[bis(1-methylethyl)amino]sulfonyl]carbamate,
2,6-Bis(1-methylethyl)phenyl[[(1-methylethyl)phenylmethyl)amino]sulfonyl]carbamate,
2,6-Bis(1-methylethyl)phenyl[(hexylamino)sulfonyl]carbamate,
2,6-Bis(1-methylethyl)phenyl[(dioctylamino)sulfonyl]carbamate,
2,6-Bis(1-methylethyl)phenyl[[cyclo-hexyl (1-methylethyl)amino]sufonyl]carbamate,
2,6-Bis(1-methylethyl)phenyl[(methyloctylamino)sulfonyl]carbamate,
2,6-Bis(1-methylethyl)phenyl[(dihexylamino)sulfonyl]carbamate,
2,6-Bis(1-methylethyl)phenyl ester(4-morpholinylsulfonyl)carbamic acid,
2,6-Bis(1-methylethyl)phenyl ester(1-piperidinylsulfonyl)carbamic acid,
2,6-Bis(1-methylethyl)phenyl ester(1-pyrrolidinylsulfonyl)carbamic acid,
2,6-Bis(1-methylethyl)phenyl ester, monohydrochloride[(4-methyl-1-piperazinyl)sulfonyl]carbamic acid,
2,6-Bis(1-methylethyl)-phenyl ester[(2,3-dihydro-1H-indol-1-1-yl)sulfonyl]carbamic acid,
2,6-Bis(1-methylethyl)phenyl[(dibutylamino)sulfonyl]carbamate monosodium salt,
[1,1:3',1''-Terphenyl]-2'-yl[[[2,6-bis(1-methylethyl)phenyl]amino]sulfonyl ]carbamate, and
2,6-Bis(1,1-dimethylethyl)phenyl[[(diphenylmethyl)amino]sulfonyl]methyl carbamate.

* * * * *

UNITED STATES PATENT AND TRADEMARK OFFICE
CERTIFICATE OF CORRECTION

PATENT NO. : 5,254,715
DATED : October 19, 1993
INVENTOR(S) : Picard, et. al.

It is certified that error appears in the above-indentified patent and that said Letters Patent is hereby corrected as shown below:

Column 25, line 1, "-$(CH_2)_2$-Q" should read "-$(CH_2)_s$-Q".

Column 25, line 1, "form" should read "from".

Column 25, line 2, "4-" should read "5-".

Column 25, line 44, "form" should read "from".

Column 26, line 16, "form" should read "from".

Column 26, line 57, "[k(diphenyl-" should read "[[(diphenyl".

Column 27, line 7, "[k[bis-3-" should read "[[[bis-3-".

Column 28, line 21, delete the first "-1" after "indole".

Signed and Sealed this

Seventh Day of June, 1994

Attest:

BRUCE LEHMAN

*Attesting Officer*  *Commissioner of Patents and Trademarks*